United States Patent [19]

Sano et al.

[11] Patent Number: 5,617,156
[45] Date of Patent: Apr. 1, 1997

[54] FUNDUS CAMERA

[75] Inventors: Eiichi Sano; Hiroshi Minegishi, both of Tokyo, Japan

[73] Assignee: Kabushiki Kaisha Topcon, Tokyo, Japan

[21] Appl. No.: 386,350

[22] Filed: Feb. 10, 1995

Related U.S. Application Data

[63] Continuation of Ser. No. 162,799, Dec. 7, 1993, abandoned, which is a continuation of Ser. No. 798,334, Nov. 26, 1991, abandoned.

[30] Foreign Application Priority Data

Nov. 27, 1990 [JP] Japan ................... 2-323718

[51] Int. Cl.⁶ .................. A61B 3/14; A61B 3/10
[52] U.S. Cl. ............. 351/214; 351/206; 351/213
[58] Field of Search ................... 351/206, 213, 351/214, 205–208, 211, 221, 246; 259/738–740, 227; 354/62; 250/458.1

[56] References Cited

U.S. PATENT DOCUMENTS

| 4,265,518 | 5/1981 | Matsumura | 351/213 |
|---|---|---|---|
| 4,422,736 | 12/1983 | Nunokawa | 351/214 |
| 4,439,024 | 3/1984 | Ito | 351/207 |
| 4,799,783 | 1/1989 | Takahashi et al. | 351/206 |
| 4,810,084 | 3/1989 | Nyui | 351/206 |
| 4,859,051 | 8/1989 | Fukuma et al. | 351/211 |
| 5,039,214 | 8/1991 | Nagata et all. | 359/368 |
| 5,214,454 | 5/1993 | Sano | 351/206 |

*Primary Examiner*—Thong Nguyen
*Attorney, Agent, or Firm*—Finnegan, Henderson, Farabow, Garrett & Dunner, L.L.P.

[57] ABSTRACT

A fundus camera, for taking photographs by fluorescence, has an illuminating optical system to illuminate a fundus. The illuminating optical system is provided with a diaphragm that can be adjusted to modify the illumination state of the fundus according to the light reflected from the fundus when taking photographs by fluorescence. As a result, a good photographic image of the fundus can always be obtained.

2 Claims, 3 Drawing Sheets

FUNDUS CAMERA

This application is a continuation, application of Ser. No. 08/162,799, filed on Dec. 7, 1993, now abandoned, which is a continuation of abandoned application Ser. No. 07/798,334, filed Nov. 26, 1991, now abandoned.

BACKGROUND OF THE INVENTION

1. Field of the Invention

This invention concerns the improvement of a fundus camera which can take photographs by infra-red excited fluorescence.

2. Description of the Prior Art

Conventionally, a fundus camera is known which can take photographs by infra-red excited fluorescence, photographs by visible light excited fluorescence, and photographs other than those taken by fluorescence.

This fundus camera is provided with an illuminating optical system which illuminates a fundus with illuminating light, the range of illumination being determined by a field diaphragm in the illuminating optical system, and which photographs an image of the fundus within the predetermined range.

However, if a fundus disorder such as a block in a retinal blood vessel due to bleeding should occur when taking a photograph by fluorescence, the amount of fluorescent agent in the part of the fundus affected by bleeding decreases leading to a reduced fluorescence so that a good image is not obtained when a photograph is taken.

To increase the fluorescence, the amount of light emitted by the illuminating light source could be increased.

However, if the amount of light emitted by the illuminating light source is increased, although the brightness of the fluorescence in the part of the fundus affected by bleeding increases to a suitable level for the purpose of taking a photograph, the brightness of the fluorescence from other parts of the fundus becomes too intense so that a clear photographic image is not obtained.

In addition, deterioration of the image in the part of the fundus affected by bleeding could not be avoided.

SUMMARY OF THE INVENTION

It is therefore an object of this invention to provide a fundus camera wherein, by modifying the state of the illuminating light on the fundus on the basis of a fundus disorder, a suitable fluorescence is produced even in the presence of such a disorder so that a good photographic image of the fundus is obtained.

The fundus camera of this invention which is equipped with an optical system to illuminate a fundus, is characterized in that the illuminating optical system is provided with an illumination field diaphragm that can vary the state of illumination of the fundus.

The range of illumination can be modified by this diaphragm. By modifying the state of illumination in accordance with a fundus disorder, a suitable fluorescence is produced even in the presence of the disorder so that a good photographic image of the fundus is obtained.

These and other objects, features and advantages of the present invention will be well appreciated upon reading of the following description of the invention when taken in conjunction with the attached drawings with understanding that some modifications, variations and changes of the same could be made by the skilled person in the art to which the invention pertains without departing from the spirit of the invention or the scope of the claims appended hereto.

BRIEF DESCRIPTION OF THE ATTACHED DRAWINGS

DESCRIPTION OF THE PREFERRED EMBODIMENTS

An embodiment of the fundus camera of the invention will now be described with reference to the drawings.

This fundus camera can take photographs by infra-red excited fluorescence, photographs by visible light-excited fluorescence and photographs other than those taken by fluorescence, however in the present embodiment the case where infra-red excited fluorescence is used to take a photograph will be described.

Figure 1:
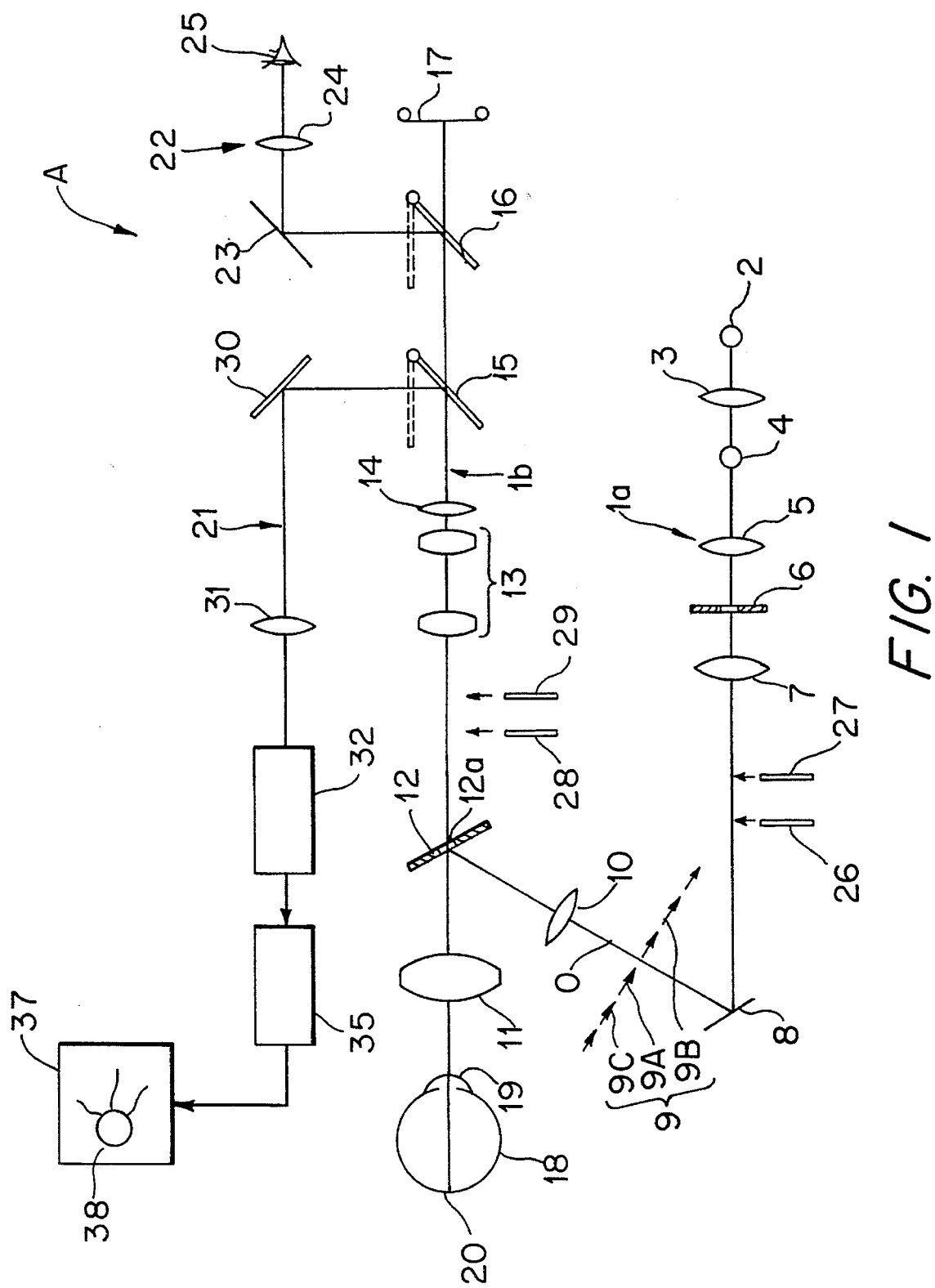
FIG. 1 is a schematic drawing illustrating the fundus camera of this invention in its entirety.

In the fundus camera A shown in FIG. 1, 1a is an illuminating optical system and 1b is a photographic optical system.

The illuminating optical system 1a broadly comprises a halogen lamp 2 as an observation optical source, a condensing lens 3, a xenon lamp 4 as a photographic optical source, a condensing lens 5, an annular diaphragm 6, a relay lens 7, a mirror 8, an illumination field diaphragm 9, and a relay lens 10.

The photographic optical system 1b comprises an objective lens 11, a holed mirror 12, a focusing lens 13, an imaging lens 14, a quick return mirror 15, a quick return mirror 16 and a film 17, an objective lens 11 being situated facing the subject's eye 18.

The annular diaphragm 6 is situated in a conjugate position to the pupil 19 of the subject's eye 18 with respect to the relay lenses 7 and 10, and the objective lens 11.

The illumination field diaphragm 9 is situated such that it is free to move along the optic axis 0 of the optical path of the illumination optical system 1a, and is moved to a conjugate position with respect to the fundus 20 of the subject's eye 18.

By freely varying the position of the diaphragm 9 and adjusting its aperture, the illumination field can be changed and any desired part of the fundus 20 can be illuminated with light.

Figure 2A:
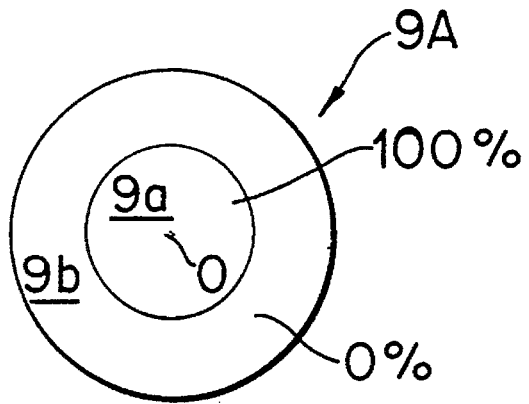
FIGS. 2a–2c show different embodiments of an illumination field diaphragm of the fundus camera of this invention.
Figure 2B:
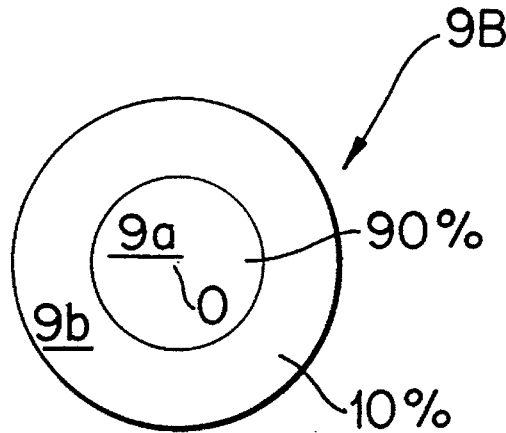
Figure 2C:
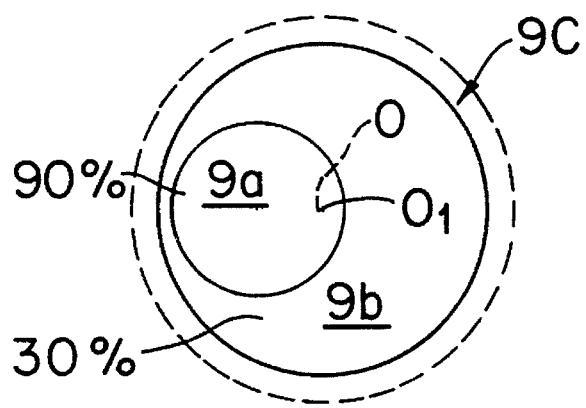

As shown in FIGS. 2a–2c, the transmittance of this illumination field diaphragm 9 with respect to infra-red light is different in its central region 9a and peripheral region 9b. Various types of the diaphragm 9 may thus be provided, for example a diaphragm wherein the central region 9a has 100% transmittance and the peripheral region 0% transmittance (9A), a diaphragm wherein the central region 9a has 90% transmittance and the peripheral region 9b 10% transmittance (9B), or a diaphragm wherein the central region has 30% transmittance and the peripheral region 50% transmittance as may be necessary.

Further, various types may be provided wherein the central region 9a is decentered from the optic axis 0, of the illumination field diaphragm 9 (9C).

Further, various types may be provided wherein the area of the central region 9a is different.

In this manner, by making the transmittance of the central region 9a and peripheral region 9b different, or by making the position or area of the illuminating area different, an increase in the amount of light may be avoided in parts where it is not needed even if the amount of light from the illuminating optical source is increased overall.

Figure 3:
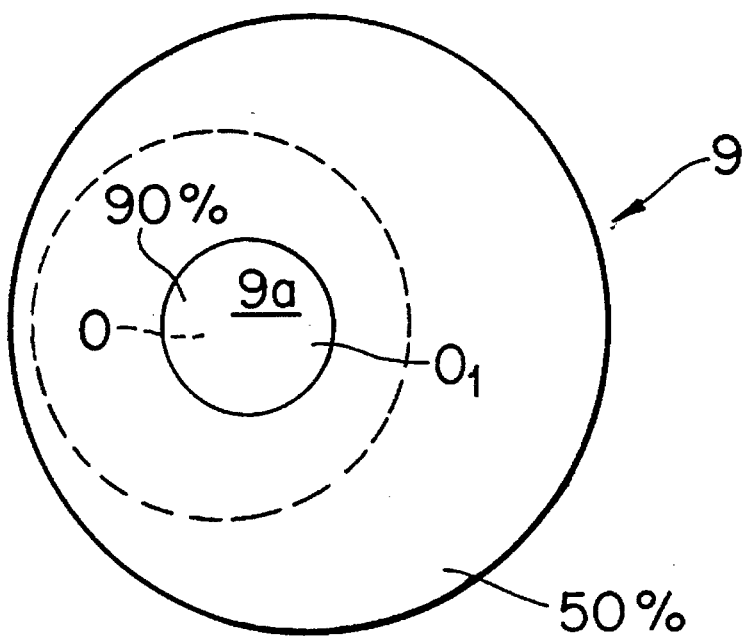
FIG. 3 is a schematic view of an example wherein the illumination field diaphragm has been displaced with respect to the optical axis of an optical path of the illuminating system of the camera.

Further, as shown in FIG. 3, the illuminating field diaphragm 9 may be installed such that its optic axis 0, can be displaced with respect to the optic axis 0 of the optical path of the illuminating optical system 1a.

By adjusting the illuminating field diaphragm 9, therefore, any transmittance and illuminating position or area may be selected and the diaphragm 9 positioned in the optical path of the illuminating optical system 1a so as to modify the illumination field and state as desired.

When making an observation, illuminating light from the halogen lamp 2 is guided via the condensing lenses 3, 5, annular diaphragm 6, relay lens 7, mirror 8, illumination field diaphragm 9, relay lens 10, holed mirror 12 and objective lens 11 to the subject's eye 18 so as to illuminate the fundus 20 of the eye 18. When this illuminating light passes through the pupil 19 of the subject's eye 18, it becomes ring-shaped.

When taking a photograph, the xenon lamp 4 is turned on by a switch, not shown, and the fundus 20 is illuminated as when making an observation.

The light beam from the fundus 20 is guided via the objective lens 11 to the holed mirror 12, and via a hole 12a of the holed mirror 12, the focusing lens 13 and imaging lens 14 to the quick return mirror 15.

When making an observation and/or taking a photograph under visible light, the quick return mirror 15 is removed from the optical path of the photographic optical system 1b. When making an observation and/or taking a photograph under infra-red light, the quick return mirror 15 is inserted in the optical path of the photographic optical system 1b. This quick return mirror 15 forms part of a television image receiving system 21 which will be described hereinafter.

When making an observation for the purpose of taking a photograph under visible light, the quick return mirror 16 is inserted in the optical path of the photographic optical system 1b. The light beam from the fundus 20 is reflected by this quick return mirror 16, and then enters a subject's eye 25 via a mirror, 23 and eyepiece 24 of an eyepiece optical system 22.

These procedures permit observation of the fundus 20 of a subject's eye 18.

An exciter filter 26 for use with visible light excited fluorescence, and an exciter filter 27 for use with infra-red light excited fluorescence, may be inserted in the optical path of the illuminating optical system 1a between the mirror 8 and the relay lens 7. Further, a barrier filter 28 for use with visible light excited fluorescence, and a barrier filter 29 for use with infra-red light excited fluorescence, may be inserted in the optical path of the photographic optical system 1b between the holed mirror 12 and the focusing lens 13.

When taking a color photograph by visible light, the exciter filter 26 and exciter filter 27 are removed from the optical path of the illuminating optical system 1a, and the barrier filter 28 and barrier filter 29 are removed from the optical path of the photographic optical system 1b.

When taking a photograph by visible light-excited fluorescence, the exciter filter 26 is inserted in the optical path of the illuminating optical system 1a, and the barrier filter 28 is inserted in the optical path of the photographic optical system 1b.

When taking a photograph by infra-red light excited fluorescence (wavelength 800 nm–950 nm), the exciter filter 27 is inserted in the optical path of the illuminating optical system 1a, and the barrier filter 29 is inserted in the optical path of the photographic optical system 1b.

The television image receiving system 21 comprises a polarizing mirror 30, television relay lens 31 and a CCD camera 32 as a photographic device. The photoelectrically converted output of the CCD camera 32 is input to a processing circuit 35, and the circuit 35 outputs an image signal based on the photoelectrically converted signal to a television monitor 37. Based on this image signal, the television monitor 37 may display for example a fundus image 38.

When taking a color photograph by visible light or a photograph by visible light excited fluorescence, the xenon lamp 4 is turned on by a switch, not shown, the fundus 20 is illuminated, the quick return mirror 16 is simultaneously removed from the optical path of the photographic optical system 1b so as to guide the light beam from the fundus 20 to the film 17 where recording takes place.

Figure 4:
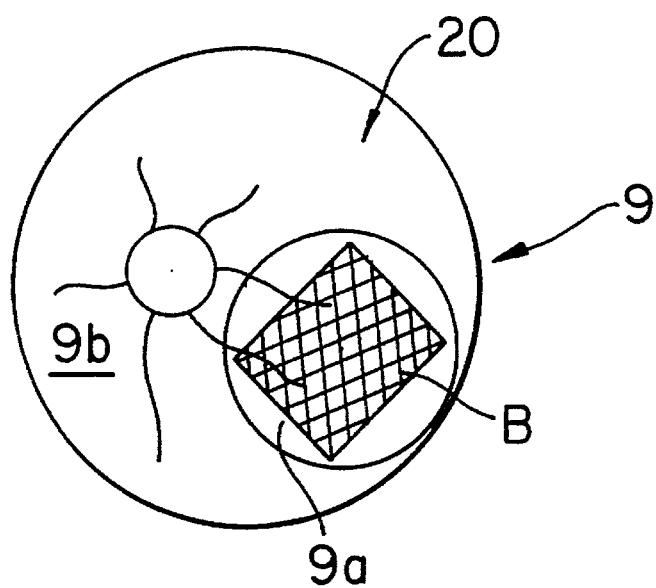
FIG. 4 is a schematic view of the correspondence of different positions of the illumination field diaphragm with different positions of a fundus when a fundus disorder occurs.

When taking a photograph by infra-red light excited fluorescence or by visible light excited fluorescence, if a fundus disorder such as a block in a retinal blood vessel due to bleeding should occur as shown in FIG. 4, the illumination field is changed by adjusting the illumination field diaphragm 9 so as to illuminate a desired part of the fundus 20.

By changing the illumination field, the illumination can be increased only of that part B of the fundus which is affected by bleeding which would otherwise lead to a decreased fluorescence preventing a good photographic image from being obtained, and the intensity of the fluorescence of the part B alone can thus be increased.

Even if the amount of light from the illuminating optical source is increased overall to obtain an intensity suitable for photographing the bleeding part B, therefore, increase of light in parts other than the part B can be prevented and a clear photographic image is obtained.

In the aforesaid embodiment, the illumination field diaphragm 9 was installed such that it could be freely moved along the optic axis 0 of the illuminating optical system 1a, and such that its optic axis 0, could be displaced with respect to the optic axis 0 of same. It is however possible to provide an illuminating diaphragm which is fixed with respect to the optic axis of the illuminating optical system 1a and which does not permit the illuminating field to be changed, together with for example a rotary type illumination diaphragm for use with infra-red light excited fluorescence which rotates so as to select a desired transmittance or range of illumination and which is mounted on the fixed diaphragm.

This rotary type illumination diaphragm, as in the case of the illumination field diaphragm 9 of the aforesaid embodiment, may for example comprise parts having a central region 9a and a peripheral region 9b with a different transmittance to infra-red light, or parts having a central region 9a of different area, or parts having a central region 9a which is decentered with respect to the optic axis 01 of the diaphragm 9, or it may be installed such that its optic axis is displaced with respect to the optic axis 0 of the optical path of the illuminating optical system 1a.

By mounting this rotary type illumination diaphragm on an illuminating diaphragm which does not permit the illuminating field to be changed, therefore, it is still possible to change the illuminating field so as to vary the illumination state as desired when taking a photograph by infra-red light excited fluorescence.

What is claimed is:

1. A fundus camera comprising:

an illuminating optical system for illuminating a fundus for observation and for exciting a fluorescent agent therein to enable taking a photograph of the fundus by fluorescence;

said illuminating optical system having an optical path and comprising:

an illumination field diaphragm, disposed at a position substantially conjugate with the fundus, having regions each being of predetermined size, shape, and disposition with different respective transmittances of light; and said illumination field diaphragm being displaceable in the optical path of said illuminating optical system and in a direction perpendicular to the optical path and thereby being disposed in the optical path so that a region of said diaphragm with a higher transmittance corresponds to a disordered part of the fundus and a region of said diaphragm with a lower transmittance corresponds to parts of said fundus other than said disordered part.

2. A fundus camera as defined in claim 1, wherein the transmittance of said illumination field diaphragm in a central region of said diaphragm is higher than that in a peripheral region thereof.

* * * * *